(12) United States Patent　　(10) Patent No.: US 8,944,983 B2
Nguyen et al.　　(45) Date of Patent: Feb. 3, 2015

(54) MULTI-UNIT BLOOD PROCESSOR WITH ISOLATED VALVES FOR RADIO FREQUENCY SEALING

(75) Inventors: Hong Duc Nguyen, Lafayette, CO (US); Bruce Ellingboe, Littleton, CO (US); Darryl Hudock, Highlands Ranch, CO (US)

(73) Assignee: Terumo BCT, Inc., Lakewood, CO (US)

( * ) Notice: Subject to any disclaimer, the term of this patent is extended or adjusted under 35 U.S.C. 154(b) by 927 days.

(21) Appl. No.: 13/110,548

(22) Filed: May 18, 2011

(65) Prior Publication Data

US 2011/0312481 A1　　Dec. 22, 2011

Related U.S. Application Data

(60) Provisional application No. 61/355,917, filed on Jun. 17, 2010.

(51) Int. Cl.
*B04B 7/00* (2006.01)
*B04B 5/04* (2006.01)
*A61M 1/02* (2006.01)
(Continued)

(52) U.S. Cl.
CPC ............ *B04B 5/0428* (2013.01); *A61M 1/0209* (2013.01); *A61M 1/3693* (2013.01); *B04B 13/00* (2013.01); *A61M 1/0218* (2013.01); *A61M 1/3698* (2013.01)
USPC ................................................ 494/45; 494/2

(58) Field of Classification Search
CPC ...... B04B 5/0428; B04B 5/0442; B04B 15/00
USPC ............................. 494/1, 2, 5, 10, 43, 45, 84; 604/4.01–6.16; 210/781, 782, 787; 422/533, 537, 540
See application file for complete search history.

(56) References Cited

U.S. PATENT DOCUMENTS

| | | | |
|---|---|---|---|
| 3,427,896 | A | 2/1969 | Hartman, Jr. |
| 3,812,724 | A | 5/1974 | Curtz et al. |
| 3,921,898 | A | 11/1975 | Finkel |

(Continued)

FOREIGN PATENT DOCUMENTS

| | | | |
|---|---|---|---|
| EP | 0536594 | A1 | 4/1993 |
| EP | 0578086 | A1 | 1/1994 |

(Continued)

OTHER PUBLICATIONS

Dow-Key Microwave Catalog. <http://www.dowkey.com/_upload/DowKeyCatalog.pdf>. Last modified May 30, 2003.*

(Continued)

*Primary Examiner* — Timothy Cleveland
(74) *Attorney, Agent, or Firm* — René A. Pereyra (57) ABSTRACT

An apparatus for separating at least two discrete volumes of a composite liquid into components, comprising a valve design that facilitates loading and unloading of sets of blood bags. The valves comprise a jaw mounted on a shaft, the jaw being adapted to apply radio frequency energy to seal a tube, a stepper motor section, and at least two position sensors. The valve sections are mounted on an upper plate, and the stepper motor sections are mounted on a lower plate. A main radio frequency coil is selectively electrically coupled to each of the valves through a multiplexing switch.

8 Claims, 7 Drawing Sheets

(51) Int. Cl.
　　*A61M 1/36*　　(2006.01)
　　*B04B 13/00*　　(2006.01)

(56) References Cited

U.S. PATENT DOCUMENTS

| | | | |
|---|---|---|---|
| 3,945,380 A | | 3/1976 | Dabney et al. |
| 4,052,661 A | * | 10/1977 | Higham et al. ............... 324/322 |
| 4,157,781 A | | 6/1979 | Maruyama |
| 4,295,386 A | | 10/1981 | Zhivotov |
| 4,901,754 A | * | 2/1990 | Sable et al. .................. 251/332 |
| 4,919,646 A | | 4/1990 | Perdriat |
| 5,715,731 A | | 2/1998 | Koch |
| 6,652,475 B1 | | 11/2003 | Sahines et al. |
| 6,837,485 B2 | | 1/2005 | Kawasaki |
| 6,852,074 B1 | | 2/2005 | Jorgenson et al. |
| 6,910,998 B2 | | 6/2005 | Eberle |
| 6,953,084 B2 | | 10/2005 | Greeb et al. |
| 7,143,993 B2 | * | 12/2006 | Everingham et al. ........... 251/77 |
| 7,166,217 B2 | | 1/2007 | Holmes et al. |
| 7,241,281 B2 | | 7/2007 | Coelho et al. |
| 7,413,665 B2 | | 8/2008 | Holmes et al. |
| 7,425,192 B2 | | 9/2008 | Sacco et al. |
| 7,438,679 B2 | | 10/2008 | Hlavinka et al. |
| 7,648,639 B2 | | 1/2010 | Holmes et al. |
| 7,674,221 B2 | | 3/2010 | Hudock et al. |
| 7,819,793 B2 | | 10/2010 | Menhennett et al. |
| 2007/0209716 A1 | * | 9/2007 | Rankin ........................... 251/65 |
| 2008/0147240 A1 | | 6/2008 | Hudock et al. |
| 2008/0220959 A1 | | 9/2008 | Holmes et al. |
| 2010/0210441 A1 | | 8/2010 | Dolecek |
| 2011/0003675 A1 | | 1/2011 | Dolecek |
| 2011/0136645 A1 | | 6/2011 | Ellingboe et al. |

FOREIGN PATENT DOCUMENTS

| | | |
|---|---|---|
| EP | 0643975 A1 | 3/1995 |
| EP | 1736186 A1 | 12/2006 |
| WO | 00/54823 A1 | 9/2000 |
| WO | 2006/054828 A1 | 5/2006 |

OTHER PUBLICATIONS

PCT/US2011/036979, "International Search Report", mailed Nov. 23, 2011.
PCT/US2011/036979, "Written Opinion", mailed Nov. 23, 2011.
PCT/US2011/036979, "Partial International Search Report", mailed Sep. 16, 2011.
EP06076188.9: "Extended European Search Report", Feb. 14, 2007.

* cited by examiner

MULTI-UNIT BLOOD PROCESSOR WITH ISOLATED VALVES FOR RADIO FREQUENCY SEALING

CROSS REFERENCE TO RELATED APPLICATIONS

This application claims the benefit of U.S. Provisional Application No. 61/355,917 filed Jun. 17, 2010.

FIELD OF THE INVENTION

The present invention relates to an apparatus and a method for separating at least two discrete volumes of a blood into at least two components each.

BACKGROUND

U.S. application Ser. No. 11/954,388 filed Dec. 12, 2007 describes an apparatus for separating discrete volumes of a composite liquid such as blood into at least two components. U.S. Provisional Application No. 61/267,484 filed Dec. 8, 2009 describes a similar apparatus with rotating valves.

The apparatus and a method of the present patent application are particularly appropriate for the separation of biological fluids comprising an aqueous component and one or more cellular components. Potential uses of the invention include: extracting a plasma component and a cellular component (including platelets, white blood cells, and red blood cells) from a volume of whole blood. A component, such as washed red blood cells, may also be filtered so as to remove residual prions, white blood cells or platelets from the red blood cells.

An apparatus for processing blood components that can process at once at least two discrete volumes of a composite liquid, in particular, two unequal volumes wherein the proportions of the various components of the composite liquid that may vary from one discrete volume to another one, is known from U.S. application Ser. No. 11/954,388 and a similar apparatus with rotating valves is described in U.S. Provisional Application 61/267,484. A method is described therein for separating at least two discrete volumes of a composite liquid into at least a first component and a second component. The method comprises at least two separation bags containing two discrete volumes of a composite liquid in separation cells mounted on a rotor; storing in at least one container on the rotor at least two first component bags connected to the at least two separation bags respectively; separating at least a first and a second component in each of the separation bags; transferring at least one fraction of a first separated component into a component bag; detecting a characteristic of a component at a location in each separation bag; and stopping transferring the fraction of the first component upon detection of the characteristic of a component at the first determined location.

SUMMARY OF THE INVENTION

The present invention comprises improvements on a centrifugal blood separation device capable of processing a plurality of blood units at the same time. The improvements include a valve design with significantly fewer parts than previous designs, for example U.S. Provisional Application 61/267,484. Reduction in the number of parts is a significant advantage in a multi-unit blood processor, wherein each set of bags for processing a unit of blood uses three or more valve, all mounted on a centrifuge rotor. A blood processor that can simultaneously process four units of blood, for example, might have twelve or more valves mounted on the central rotator. The valves of this invention comprise a non-rotating head, mounted on a non-rotating shaft. The head is driven to a "closed" position by spring loading. The head may also be raised into an "open" position from time to time by the action of a shaft-activating stepper motor. When the head is in the closed position, blood or blood components cannot flow through a tube placed in the valve.

The head may also convey radio frequency energy to the tube to seal and sever the tube. The valve apparatus comprises means for maintaining a constant pressure on the tube and contact with the tube as the tube is melted and sealed. The constant pressure means may comprise a pre-loaded spring or similar structure, such as a pre-loaded pneumatic actuator. The valve mechanically and electrically disconnects the shaft and head from a stepper motor during radiofrequency (RF) welding that seals the tube. A primary radio frequency coil is coupled to a plurality of valve heads through a switching manifold. In one embodiment, all available valve heads are coupled to a single primary radio frequency coil. Supplemental balancing coils may be provided between the switching manifold and each of the valve heads.

In addition, an asymmetrical junction in the blood bag and tubing set inhibits errors when the bags and tubes are loaded into the device. A grip or handle is provided on the asymmetric junction to assist an operator loading the device.

According to the present invention, an apparatus is provided for separating at least two discrete volumes of a composite liquid into at least a first component and a second component, the apparatus comprising a centrifuge having a rotor with a rotation axis, at least two separation cells mounted on the rotor, each cell adapted to receive a separation bag containing a volume of composite liquid, such as blood; and at least one sensor associated with each separation cell for generating information related to a characteristic of a component separated in a separation bag within the separation cell; and a control unit programmed for receiving information generated by the at least one sensor associated with each separation cell; and for controlling rotation speed in view of information generated by one of the at least one sensor associated with each of the at least two separation cells. The apparatus is adapted to receive a disposable set of tube-connected bags. The disposable set preferably comprises a primary bag, initially containing whole blood, fluidly connected to at least one (preferably two) component bag for receiving blood components such as plasma or platelets. A discard or waste bag may also be provided. The disposable set may further comprise a red blood cell collection bag fluidly connected to the primary bag through a filter.

The apparatus comprises a plurality of valves associated with each separation cell. The valves comprise at least one valve adapted to control fluid flow into the at least one component bag, more preferably two valves where two component bags are provided, each component valve being associated with a component bag. The valves may further comprise a discard valve for controlling fluid flow of used wash solution into the wash solution discard bag.

The disposable set comprises an asymmetrical junction joining a plurality of tubes of the bag set. The asymmetrical junction can be mounted on the rotor (which carries the valves) in a single orientation only. Such an action brings the tubes of the disposable set into proximity with appropriate valves. The bag set can be quickly and unambiguously mounted on the apparatus with less potential for operator error. A handle or grip on the asymmetrical junction helps an operator insert the junction and its associated tubes into the apparatus.

Other features of the apparatus include a control unit programmed for causing the rotor to rotate at a sedimentation speed for separating a least two components in at least two primary or separation bags contained in the at least two separation cells respectively; causing at least one valve associated with each separation cell to allow a flow of fluid between each separation bag and the component bag connected thereto; causing the component transferring means to transfer at least a portion of a separated component from each of the at least two separation bags into the component bag connected thereto; and causing at least one valve associated with each separation cell to block a flow of fluid between the separation bag within the separation cell and the component bag connected thereto, when the sensor associated with the separation cell detects the characteristic of a separated component. The control unit may also slow the rotor, cause hydraulic fluid to be pulled from bladders adjacent the primary bags, and open wash valves, thereby allowing wash solution to flow into the primary bag. The control unit then causes additional hydraulic fluid to be withdrawn from the bladders, whereby a free fluid surface is created within the primary bag. The control unit may cause the rotor to oscillate, thereby agitating the residual blood component and wash solution within the primary bag, and then causes the rotor to rotate at a sedimentation speed for separating the residual blood component and the wash solution. The control unit causes the wash solution discard valve to open, allowing used wash solution to flow into the wash solution discard bag. The residual blood component may be washed a plurality of times, thereby reducing levels of a cellular component or other components such as prions to a medically acceptable level.

Other features and advantages of the invention will appear from the following description and accompanying drawings, which are to be considered exemplary only.

DESCRIPTION OF EMBODIMENT

For the sake of clarity, the invention will be described with respect to a specific use, namely the separation of whole blood into at least two components, in particular into a plasma component and a red blood cell component, or into a plasma component, a platelet component and a red blood cell component. The discrete volume mentioned hereunder will typically be the volume of a blood donation. The volume of a blood donation may vary from one donor to another one (for example, 500 ml plus or minus 10% in the United States). It is also well known that the proportion of the components of blood usually varies from one donor to another one. In particular, the donor's hematocrit, which is the ratio of the volume of the red blood cells to the volume of the sample of whole blood considered, varies from one person to another. Consequently, the density of blood may slightly vary for one donor to another one. It should be understood however that this specific use is exemplary only.

Figure 1:
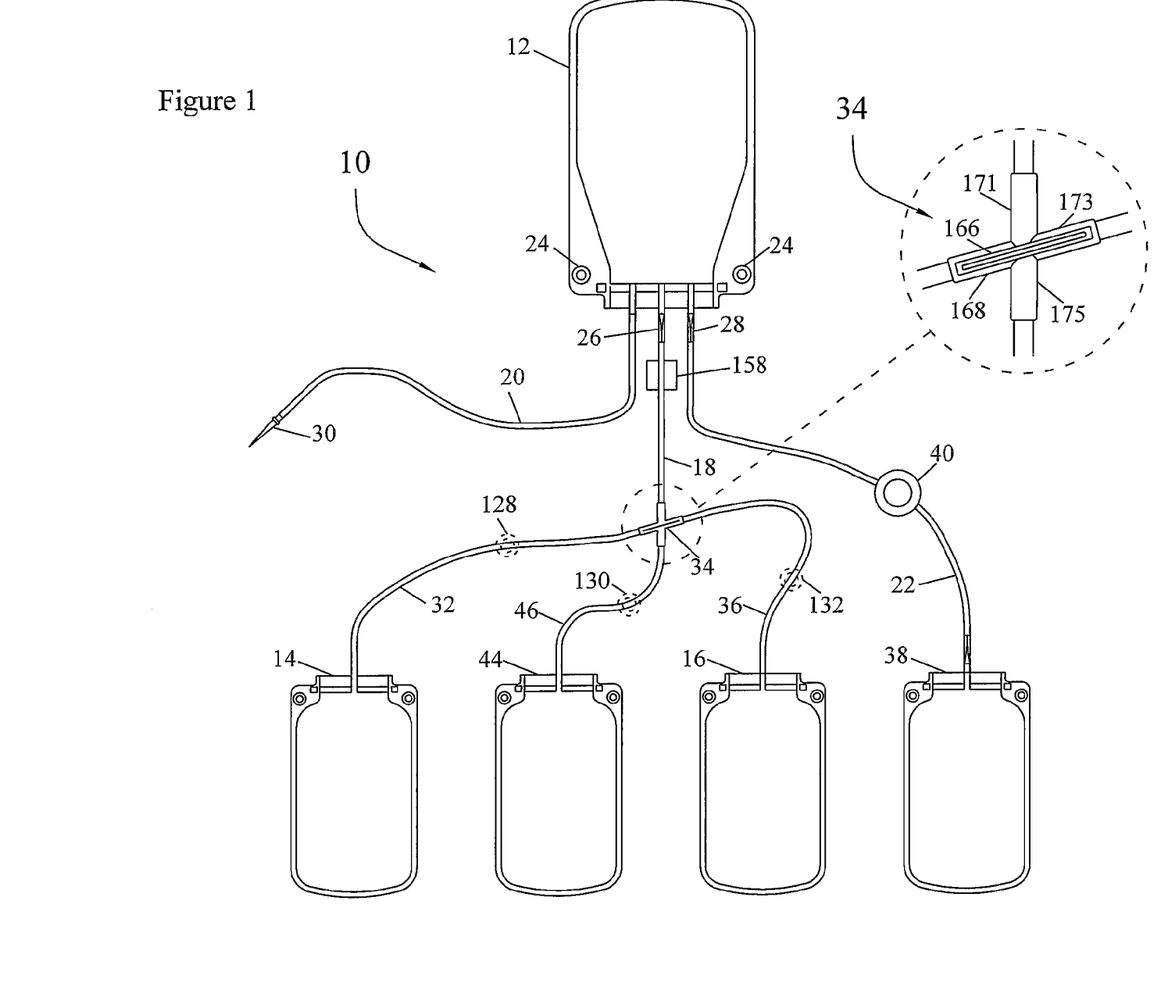
FIG. 1 is a schematic view of a first set of bags designed for cooperating with a separation apparatus.

FIG. 1 shows an example of a set 10 of bags adapted to be used for the separation of a composite liquid (e.g. whole blood) into a primary component (e.g. red blood cells) and at least one secondary component, preferably a plurality of secondary components (e.g., plasma, platelets, or both). This bag set comprises a flexible primary separation bag 12 and two flexible component bags 14, 16 connected thereto.

When the composite liquid is whole blood, the separation bag 12 has two purposes, and is successively used as a collection bag and as a separation bag. It is intended to initially receive a discrete volume of whole blood from a donor (usually about 500 ml) and to be used later as a separation chamber in a separation apparatus. The separation bag 12 is flat and generally rectangular. It is made of two sheets of plastic material that are welded together so as to define an interior space having a main rectangular portion connected to a triangular proximal portion. A first tube 18 is connected to a proximal end of the triangular portion, and a second tube 20 and a third tube 22 are connected on opposite sides adjacent the first tube 18. The proximal ends of the three tubes 18, 20, 22 are embedded between the two sheets of plastic material so as to be parallel to each other. The separation bag 12 further comprises a hole 24 in each of its two proximal corners that are adjacent to the three tubes 18, 20, 22. The holes 24 may be used to secure the separation bag to a separation cell on a centrifugal blood separation apparatus.

The separation bag initially contains a volume of anticoagulant solution (typically about 63 ml of a solution of citrate phosphate dextrose for a blood donation of about 450 ml). The first and third tubes 18, 22 are fitted at their proximal ends with a breakable stopper 26, 28 respectively, blocking liquid flow therethrough. The breakable stopper is sometimes called a "frangible". The second tube 20 is a collection tube having a needle 30 connected to its distal end. At the beginning of a blood donation, the needle 30 is inserted in the vein of a donor and blood flows into the separation bag 12. After a desired volume of blood has been collected in the separation bag 12, the collection tube 20 is sealed and cut, disconnecting the needle from the bag set 10. Alternatively, previously collected blood may be transferred to the separation bag 12 through the collection tube 20, with or without the use of the needle 30.

The first component bag 14 is intended for receiving a plasma component. The bag 14 is flat and substantially rectangular. It is connected through a plasma collection tube 32 and an X connector 34 to the first tube 18. The second component bag 16 is intended for receiving a platelet component. The second component bag 16 is also flat and substantially rectangular. It is connected through a platelet collection tube 36 and the X connector 34 to the first tube 18. A third component bag 38 is intended to receive a red blood cell component (which may be washed), from the primary bag 12. Red blood cells may be drained through tube 22, which may include a filter 40, into third component bag 38. A breakable stopper 28 or frangible in tube 22 prevents premature flow of red blood cells into the third component bag 38.

A wash solution bag 44, if used, may initially contain wash solution such as saline or a storage solution such as SAGM. Wash solution may be transferred through a wash solution tube 46 and the X connector 34 by way of the first tube 18 into the primary bag 12 when the primary bag 12 contains high hematocrit blood cells. "High hematocrit" means a percentage of red blood cell volume to total fluid volume of at least 80 percent, more preferably 90 percent, and yet more preferably 95 percent. After wash solution is mixed with high hematocrit red blood cells and subsequently separated, used wash solution may be extracted through the first tube 18, X connector 34, and discard tube 46 into a wash solution discard bag 44. The discard bag 44 could also be used to collect a relatively rare blood component, for example, mesenchymal stem cells or some white cells to reduce filter load.

Figure 2:
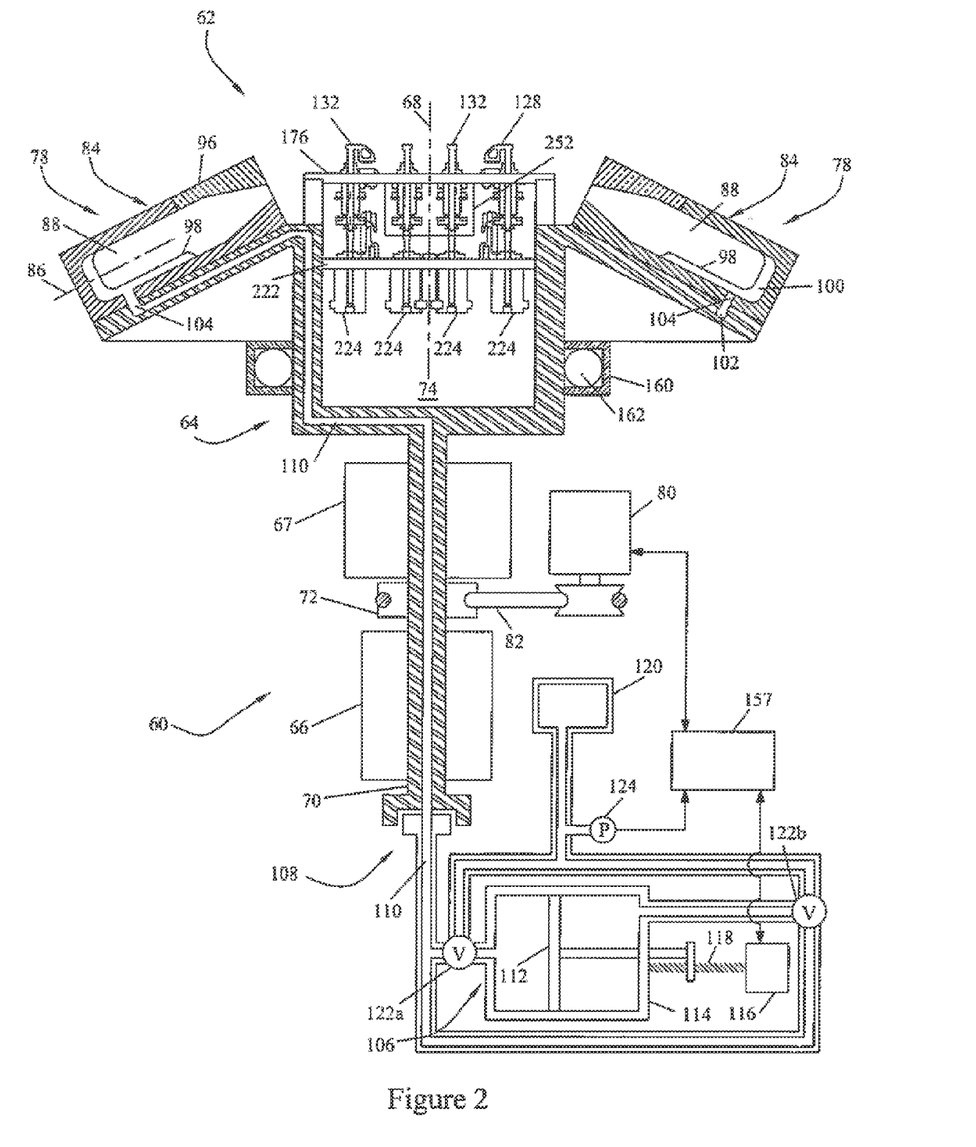
FIG. 2 is a schematic view, partly in cross-section along a diametric plane, of a first embodiment of a separation apparatus.

FIG. 2 shows an apparatus 60 for simultaneously separating by centrifugation four discrete volumes of a composite liquid. The apparatus comprises a centrifuge 62 adapted to receive four of the sets 10 of bags shown in FIG. 1, with the four discrete volumes of a composite liquid contained in the four primary separation bags 12, and a component transferring means for transferring at least one separated component from each separation bag into a component bag connected thereto. The apparatus 60 may further comprise means for washing a residual high hematocrit red blood cell component.

The centrifuge 62 comprises a rotor 64 that is supported by a bearing assembly 67 allowing the rotor 64 to rotate around a rotation axis 68. The rotor comprises a cylindrical rotor shaft 70 to which a pulley 72 is connected. A storage means comprises a central cylindrical container 74 for containing component bags, which is connected to the rotor shaft 70 at the upper end thereof so that the longitudinal axis of the rotor shaft 70 and the longitudinal axis of the container 74 coincide with the rotation axis 68. Four identical separation cells 78 are coupled to the central container 74 so as to form a symmetrical arrangement with respect to the rotation axis 68. The centrifuge further comprises a motor 80 coupled to the rotor by a belt 82 engaged in a groove of the pulley 72 so as to rotate the rotor about the rotation axis 68.

Each separation cell 78 comprises a container 84 having the general shape of a rectangular parallelepiped. The separation cells 78 are mounted on the central container 74 so that their respective median longitudinal axes 86 intersect the rotation axis 68. They are located substantially at the same distance from the rotation axis 68, and the angles between their median longitudinal axes 86 are substantially the same (i.e. 90 degrees). The median axes 86 of the separation cells 78 are inclined downwardly with respect to a plane perpendicular to the rotation axis 68.

Each container 84 comprises a cavity 88 that is so shaped and dimensioned as to loosely accommodate a separation bag 12 full of liquid, of the type shown in FIG. 1. The cavity 88 (which will be referred to later also as the "separation compartment") is defined by a bottom wall, which is the farthest to the rotation axis 68, a lower wall that is the closest to the container 74, an upper wall opposite to the lower wall, and two lateral walls. The cavity 88 comprises a main part, extending from the bottom wall, which has substantially the shape of a rectangular parallelepiped with rounded corners and edges, and an upper, or proximal, part, which has substantially the shape of a prism having convergent triangular bases. In other words, the upper part of the cavity 88 is defined by two sets of two opposing walls converging towards the central median axis 86 of the container 84. One interesting feature of this design is that it causes a radial dilatation of a thin layer of a minor component of a composite fluid (e.g. the platelets in whole blood) after separation by centrifugation, and makes the layer more easily detectable in the upper part of a separation bag. This also reduces mixing between component layers by providing a gradual, funnel-like transition into the tube. The two couples of opposite walls of the upper part of the separation cell 78 converge towards three cylindrical parallel channels (not shown), opening at the top of the container 84, and through which the three tubes 18, 20, 22 extend when a separation bag 12 is in the container 84.

The container 84 also comprises a hinged lateral lid 96, which is comprised of an upper portion of the external wall of the container 84. The lid 96 is so dimensioned as to allow, when open, an easy loading of a separation bag 12 full of liquid into the separation cell 78. The container 84 comprises a locking means (not shown) by which the lid 96 can be locked to the remaining part of the container 84. The container 84 also comprises a securing or locating means for securing or locating a separation bag 12 within the separation cell 78. The bag securing or locating means comprises two pins (not shown) protruding on the internal surface of the lid 96, close to the top of separation cell 78, and two corresponding recesses in the upper part of the container 84. The two pins are so spaced apart and dimensioned as to fit into the two holes 24 in the upper corners of a separation bag 12.

The separation apparatus further comprises a component transferring means for transferring at least one separated component from each separation bag into a component bag connected thereto. The component transferring means comprises a squeezing system for squeezing the separation bags 12 within the separation compartments 88 and causing the transfer of separated components into component bags 14, 16. The squeezing system comprises a flexible diaphragm 98 that is secured to each container 84 so as to define an expandable chamber 100 in the cavity thereof. More specifically, the diaphragm 98 is dimensioned so as to line the bottom wall of the cavity 88 and a large portion of the lower wall of the cavity 88. The squeezing system further comprises a peripheral circular manifold 102 that forms a ring. Each expansion chamber 100 is connected to the manifold 102 by a supply channel 104 that extends through the wall of the respective container 84, close to the bottom thereof. The squeezing system further comprises a hydraulic pumping station 106 for pumping a hydraulic liquid in and out the expandable chambers 100 within the separation cells 78. The hydraulic liquid is selected so as to have a density slightly higher than the density of the densest of the components in the composite liquid to be separated (e.g. the red blood cells, when the composite liquid is blood). As a result, during centrifugation, the hydraulic liquid within the expandable chambers 100, whatever the volume thereof, will generally remain in the most external part of the separation cells 78. The pumping station 106 is connected to the expandable chambers 100, through a rotary seal 108, by a duct 110 that extends through the rotor shaft 70, through the bottom and lateral wall of the central container 74, and, radially outwardly where it connects to the manifold 102. The pumping station 106 comprises a piston pump having a piston 112 movable in a hydraulic cylinder 114 fluidly connected via the rotary seal or fluid coupling 108 to the rotor duct 110. The piston 112 is actuated by a brushless DC motor 116 that moves a lead screw 118 linked to a piston rod. The hydraulic cylinder 114 is also connected to a hydraulic liquid reservoir 120 having an access controlled by two valves 122a, 122b for selectively allowing the introduction or the withdrawal of hydraulic liquid into and from a reciprocating hydraulic circuit including the hydraulic cylinder 114, the rotor duct 110 and the expandable hydraulic chambers 100. A pressure gauge 124 is connected to the hydraulic circuit for measuring the hydraulic pressure therein.

The separation apparatus further comprises four sets of three pinch valves 128, 130, 132 that are mounted on the rotor around the opening of the central container 74. Each set of pinch valves 128, 130, 132 faces one separation cell 78, with which it is associated. The pinch valves 128, 130, 132 are designed for selectively blocking or allowing a flow of liquid through a flexible plastic tube, and selectively sealing and cutting a plastic tube. Each pinch valve 128, 130, 132 comprises stepper motor and spring apparatus 134, which will be described in greater detail below, and a head 136 having a jaw 138 forming a gap in an "open" position that is defined by a stationary lower plate or anvil 178. The jaw 138 moves between an "open" position, and a "closed" position. The gap is so dimensioned that one of the tubes 18, 32, 36, 46 of the bag sets shown in FIG. 1 can be snuggly engaged therein when the jaw is in the open position. The apparatus 134 contains a mechanism for moving the jaw. The jaw 138 is connected to a radio frequency generator that supplies the energy necessary for sealing and cutting a plastic tube. The pinch valves 128, 130, 132 are mounted inside the central container 74, adjacent the interior surface thereof, so that their longitudinal axes are parallel to the rotation axis 68 and their heads protrude above the rim of the container 74. The position of a set of pinch valves 128, 130, 132 with respect to a separation bag 12 and the tubes 32, 36, 46 connected thereto when the separation bag 12 rests in the separation cell 78 associated with this set of pinch valves 128, 130, 132 is shown in dotted lines in FIG. 1. Electric power is supplied to stepper motors 224 associated with the pinch valves 128, 130, 132 through a slip ring array 66 that is mounted around a lower portion of the rotor shaft 70.

Figures 8, 9:
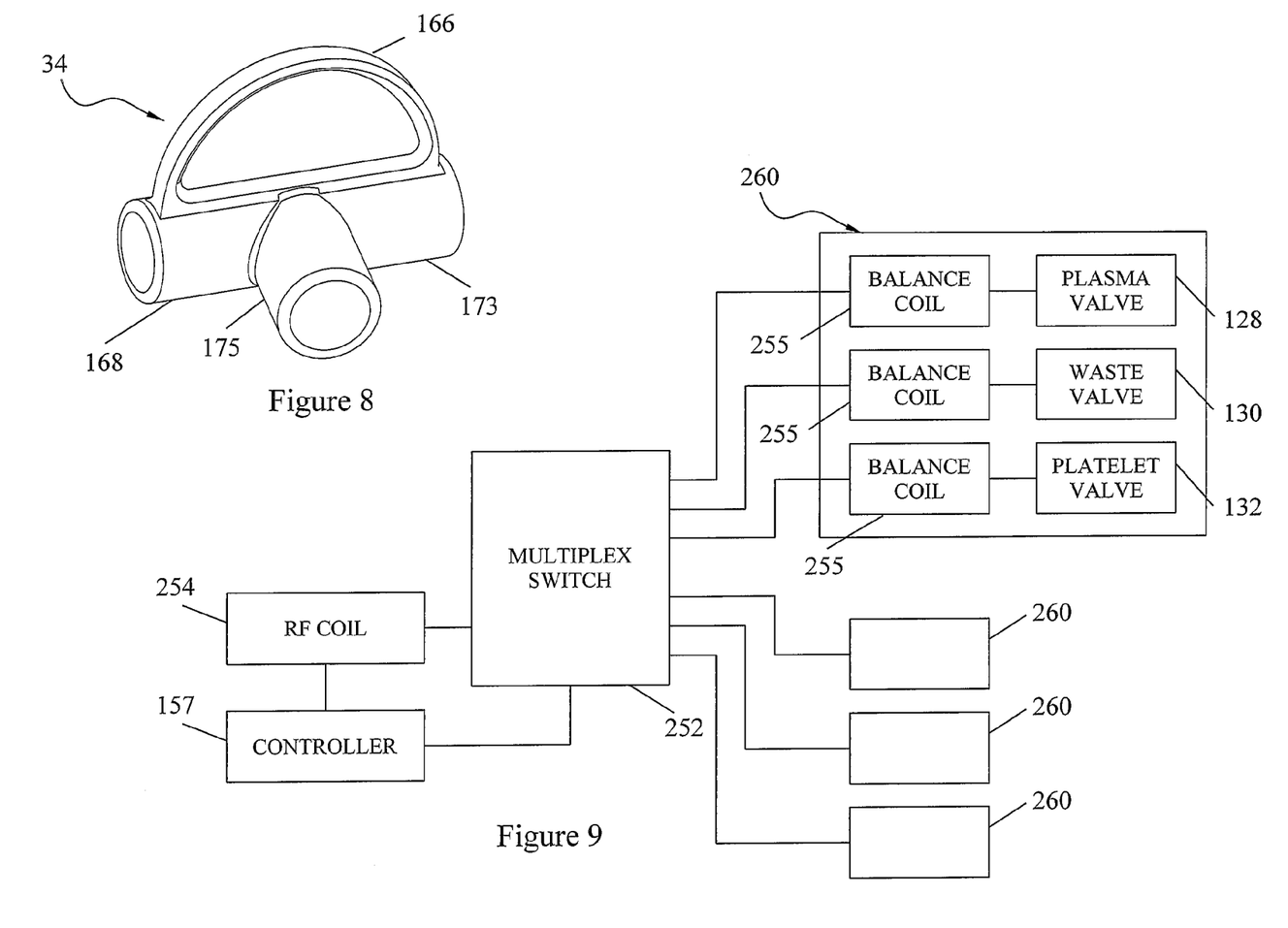
FIG. 8 is a perspective view of a connector with a handle for use in the set of bags of FIG. 1.
FIG. 9 is a schematic diagram of a radio frequency welding subsystem with multiplexing switch.

Loading a multi-unit blood separator with a plurality of bag sets 10 requires placement of tubes, such as tubes 18, 32, 36 and 46 adjacent their respective valves. Accurate placement of the tubes is enhanced by the use of the X connector or junction 34. The connector is comprised of relatively rigid plastic and forms a junction for at least three, preferably four, flexible tubes. As shown in FIG. 1 the X connector 34 comprises an "X" configuration. The "X" configuration comprises four stubs 168, 171, 173, and 175 connected to tubes 32, 18, 36, and 46, respectively. Stub 171 is coupled through tube 18 to the primary separation bag 12. Linearly across from stub 171, stub 175 connects to tube 46 and thence to the waste bag 44. Stub 168 is coupled through tube 32 to the plasma bag 14. Linearly across from stub 168, stub 173 is coupled through tube 36 to platelet bag 16. The first set of linearly aligned stubs 171, 175 and the second set of linearly aligned stubs 168, 173 are not at right angles, but form acute angles between adjacent stubs 168 and 175 and between adjacent stubs 171 and 173. This implies, of course, that oblique angles are formed between stubs 168 and 171 and between stubs 173 and 175. Because of the asymmetrical shape of the connector 34, the connector can be mounted on the central core 150 in only one direction. Each of the tubes 18, 32, 36 and 46 of the bag set 10 will consequently be reliably mounted at the proper valve 128, 130, 132 or sensor 158 (described below). The connector 34 further comprises a handle 166 (see FIG. 8), which allows the operator to more reliably place the junction and associated tubes on the central core 150. The handle may have any appropriate shape. A preferred embodiment for the handle 166 is a semi-circular fin extending linearly along linearly-disposed plasma stub 168 and platelet stub 173.

The separation apparatus also comprises a controller 157 including a control unit (e.g. a microprocessor) and a memory unit for providing the microprocessor with information and programmed instructions relative to various separation protocols (e.g. a protocol for the separation of a plasma component and a blood cell component, or a protocol for the separation of a plasma component, a platelet component, and a red blood cell component) and to the operation of the apparatus in accordance with such separation protocols. In particular, the microprocessor is programmed for receiving information relative to the centrifugation speed(s) at which the rotor is to be rotated during the various stages of a separation process (e.g. stage of component separation, stage of a plasma component expression, stage of suspension of platelets in a plasma fraction, stage of a platelet component expression, etc), and information relative to the various transfer flow rates at which separated components are to be transferred from the separation bag 12 into the component bags 14, 16. The information relative to the various transfer flow rates can be expressed, for example, as hydraulic liquid flow rates in the hydraulic circuit, or as rotation speeds of the brushless DC motor 116 of the hydraulic pumping station 106. The microprocessor is further programmed for receiving, directly or through the memory, information from the pressure gauge 124 and from four pairs of photocells (described below) and for controlling the centrifuge motor 80, the brushless DC motor 116 of the pumping station 106, and the four sets of pinch valves 128, 130, 132 so as to cause the separation apparatus to operate along a selected separation protocol.

A first balancing means initially balances the rotor when the weights of the four separation bags 12 contained in the separation cells 78 are different. The first balancing means substantially comprises the same structural elements as the elements of the component transferring means described above, namely: four expandable hydraulic chambers 100 interconnected by a peripheral circular manifold 102, and a hydraulic liquid pumping station 106 for pumping hydraulic liquid into the hydraulic chambers 100 through a rotor duct 110, which is connected to the circular manifold 102. Under centrifugation forces, the hydraulic liquid will distribute unevenly in the four separation cells 78 depending on the difference in weight of the separation bags 12, and balance the rotor.

Figure 3:
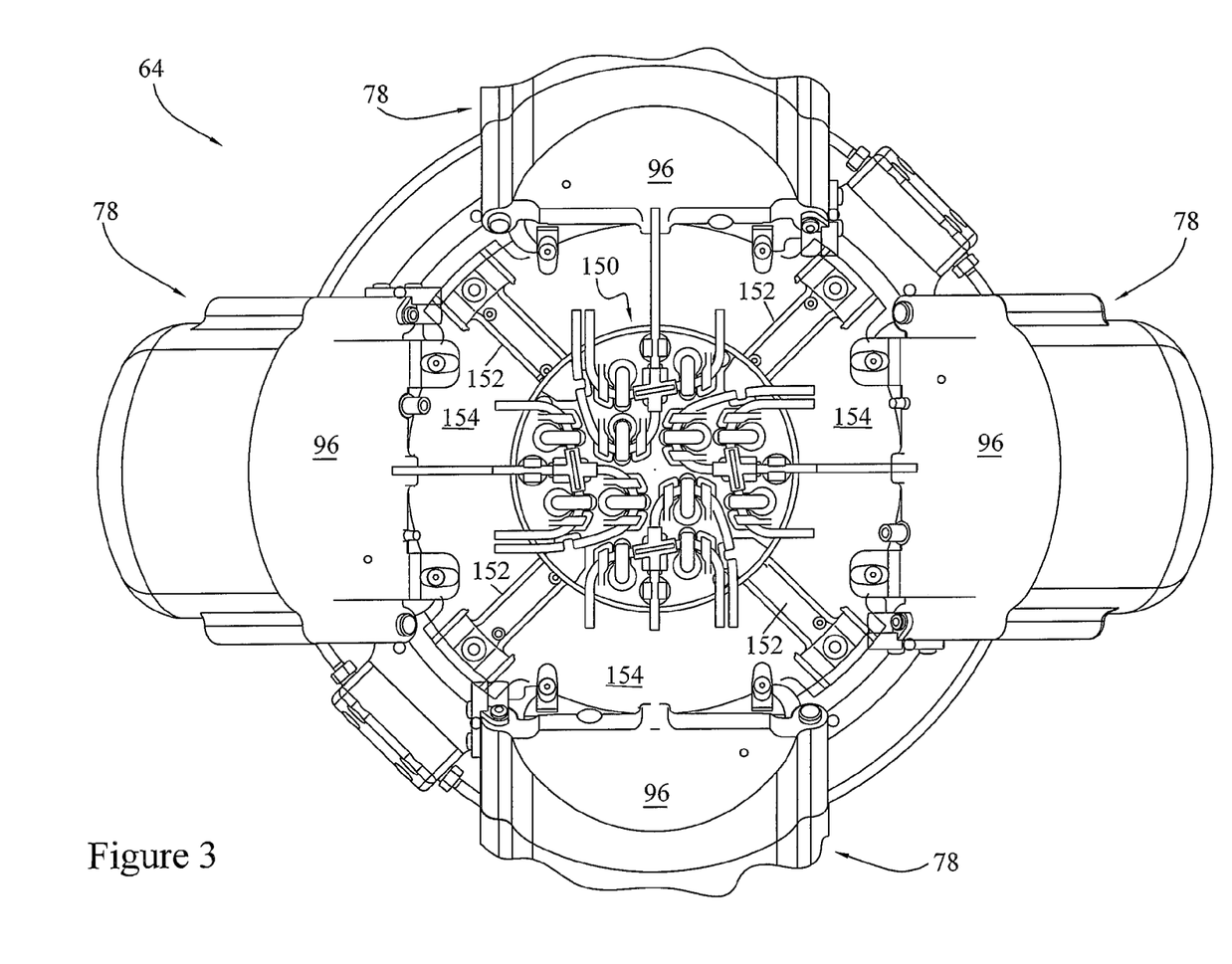
FIG. 3 is a top plan view of the separation apparatus of FIG. 2, showing at least part of four sets of bags mounted thereon.

FIG. 3 shows a top plan view of the rotor 64. Four symmetrically spaced separation cells 78 (each with a lid 96) are shown surrounding a central core 150, which contains four sets of valves 128, 130, 132 and which supports the X connector 34 and tubes of the bag sets 10. The core 150 is supported in the center of the rotor by a spider structure comprised of four radial support arms 152. The arms 152 define cavities 154 between a separation cell 78 and an adjacent set of valves 128, 130, 132 on the central core 150. The component bags 14 and 16 (for plasma and platelets respectively) and the red blood cell component bag 38, with its associated filter 40, are placed in the cavity 154 when the bag set 10 is loaded into the rotor 64. The collection and separation bag 12, which initially contains the collected unit of whole blood, is placed in the adjacent separation cell 78. The waste bag 44, which may be used for temporary fluid storage, waste fluid collection or collection of a rare or small-volume blood component, is also placed in the cavity 154 with the component bags 14, 16. FIG. 3 also shows connectors 34 having an "X" configuration, which has been explained in greater detail above.

A tube sensor 158 is able to detect the presence or absence of liquid in the tube 18 as well as to detect blood cells in a liquid. Each sensor 158 may comprise a photocell including an infrared LED and a photo-detector. Electric power is supplied to the sensors 158 through the slip ring array 66 that is mounted around the lower portion of the rotor shaft 70. In the process of separating blood into component parts, fluid components, such as plasma or platelets, are expressed out of the separation bag 12 in the separation cell 78 into component bags 14, 16 in the cavities 154. The sensor 158 may detect the presence of platelets or red blood cells. In response, the controller 157 may interrupt or change the processing for the particular set of bags where the new condition was sensed. Since the process of blood separation proceeds at different rates for different blood units, the volumes and weights of fluids in different bags and locations on the rotor will differ. A second balancing means 160 balances the rotor when the weights of the components transferred into the component bags 14, 16 in the cavities 154 are different. For example, when two blood donations have the same hematocrit and different volumes, the volumes of plasma extracted from each donation are different, and the same is true when two blood donations have the same volume and different hematocrit. The second balancing means comprises a balance assembly or ring 160, more particularly described in U.S. patent application Ser. No. 11/751,748, filed May 22, 2007, and incorporated herein by reference. The balancing apparatus of the separation apparatus comprises one or two balancing assemblies, each including a series of ponderous satellites or balls that can move freely on a specific circular orbit centered on and perpendicular to the axis of rotation of the rotor. The housing comprises a container for spherical ponderous satellites (balls) 162, which are housed in a cylindrical outer race, in which the balls slightly engage, and on which they roll, when the rotor rotates. The balancing means 160 comprises a plurality of balls. When the balls are in contact with each other, they occupy a sector of the ring of about 180 degrees. The balancing means 160 also comprises a damper or dampening fluid or element for providing resistance to the movement of the balls.

Figure 6:
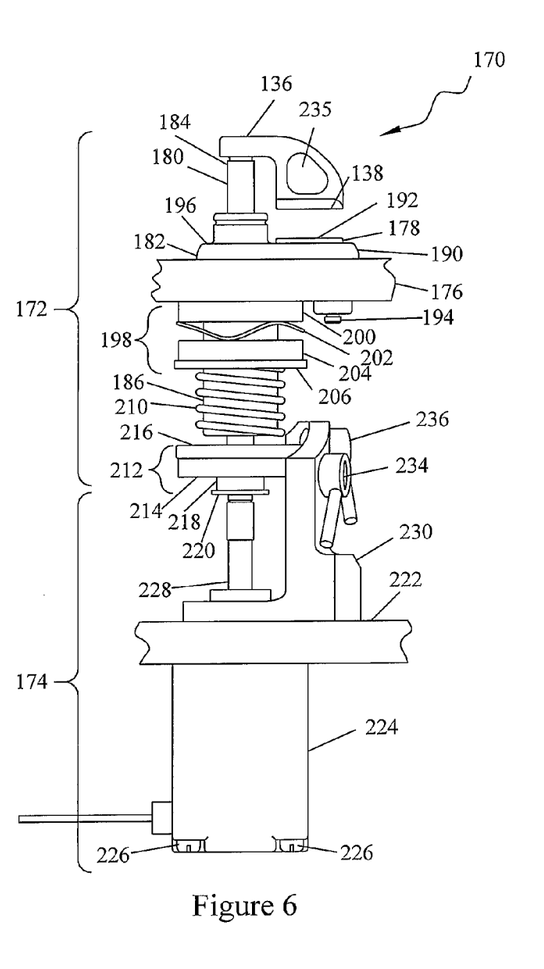
FIG. 6 is a side plan view of a valve assembly.
Figure 7:
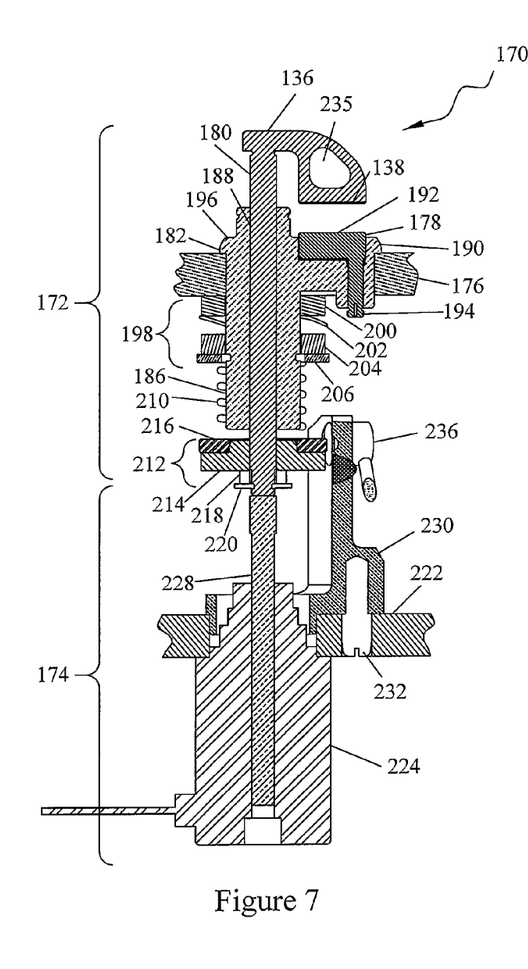
FIG. 7 is a cross-section view of the valve assembly of FIG. 6.

A valve unit 170 for valves 128, 130 and 132 is shown in FIGS. 6 and 7. The valve unit 170 comprises a spring-loaded valve section 172 and a stepper motor section 174. The stepper motor section 174 is adapted to push against the valve sections, but the two sections are not otherwise connected mechanically. Consequently, the stepper motor section can be electrically and mechanically de-coupled from the valve section. This protects the stepper motor section from transient electrical surges when radio frequency is used to seal a tube.

The valve head 136 and jaw 138 protrude through a valve cover plate 176. In either the "open" or "closed" positions or if a weld is made, the jaw 138 is centered over a welding anvil 178. The spring-loaded valve section 172 comprises a square shaft 180 mounted in a non-conducting housing 182. The valve head 136 and jaw 138 are mounted on an upper end 184 of the shaft 180. The housing 182 has a barrel 186 with a square through bore 188 in which the shaft 180 slides. The housing 182 also has a platform 190 extending from the barrel 186 and supporting the welding anvil 178. The welding anvil 178 comprises a blade 192 adapted to lie under the jaw 138 of the valve head 136. The blade is electrically coupled to a socket 194 that protrudes below the platform 190. The socket 194 can be electrically coupled to a shielded cable (not shown) that conducts radio frequency energy to the blade 192. A lip 196 circumscribing the upper end of the barrel 186 and the platform 190 allows the housing 182 to be mounted in the cover plate 176 to the limits of the lip. The housing 182 is secured to the plate by a compression assembly 198 comprising an upper washer 200, a circumferential wave spring 202, and a lower washer 204. The compression assembly 198 is held in place by an E-ring 206 that engages a circumferential slot 208 in the barrel 186. A spring 210 is mounted on the barrel 186 below the compression assembly 198. The spring 210 presses against the lower washer 204 and the E-ring 206 of the compression assembly at an upper end and against a shield assembly 212 at a lower end. The shield assembly 212 comprises a non-conducting shield 214 that supports a ferromagnetic ring 216. A spacer 218 and E-ring 220 attach the shield assembly 212 to a lower end of the square-shaft 180. The spring 210 is always in compression, to a greater or lesser degree, such that the valve section always tries to close the jaw 138 of the valve head 136 down against the blade 192. The action of the stepper motor section 174 raises the jaw 138 above the blade 192.

The stepper motor section 174 is mounted on a base plate 222 that is parallel to, but spaced apart from, the cover plate 176. The stepper motor section comprises a stepper motor 224 attached to the base plate 222 by machine screws 226. The stepper motor is electrically coupled to the controller 157 and responds to signals from the controller by raising or lowering a splined shaft 228. Raising the splined shaft 228 will push the square shaft 180 upwardly, raising the jaw 138 above the anvil 178, and opening the valve. Lowering the splined shaft 228 allows the spring 210 to push against the shaft 180 and lower the jaw 138 against either the anvil 178 or against an intervening tube. The splined shaft 228 is ordinarily lowered until there is a gap between the splined shaft 228 and the square shaft 188, even at the lowest position of the square shaft 188, which occurs when the jaw 138 contacts the anvil 178. The gap allows radio frequency energy to be applied to a tube through the anvil 178 without adversely affecting stepper motor 224. If a tube is cut and sealed by the valve, rather than simply temporarily closed, radio frequency energy would be conducted through the anvil, gradually melting the tube and simultaneously cutting and sealing the tube. As the tube melts, the spring 210 forces the jaw 138 down until the jaw meets the anvil 178, thereby keeping the tube closed throughout the cutting and sealing process.

The stepper motor section 174 further comprises a bracket 230 mounted on the base plate 222 with machine screws 232. The bracket supports a lower position sensor 234 and an upper position sensor 236 that are electrically coupled to the controller 157. The position sensors 234, 236 detect the proximity of the metallic ring 216 on the valve section 172, allowing the controller to detect the position of the jaw 138 relative to the anvil 178.

As an additional feature, the square shaft 188 and valve head 136 may be comprised of aluminum with nickel plating for improved conductivity. This reduces the weight of the shaft and valve head as compared to brass or a similar material, which reduces torsion forces acting on the valve structure in the high gravitational fields produced in the centrifuge blood separator. Moreover, to further reduce the weight, the jaw 138 may be milled out, producing a central hole 235 in the jaw 138. The hole 235 can also be manually engaged with a hook or similar tool, if it should become necessary to manually release the valve against the action of the spring 210.

Figure 4:
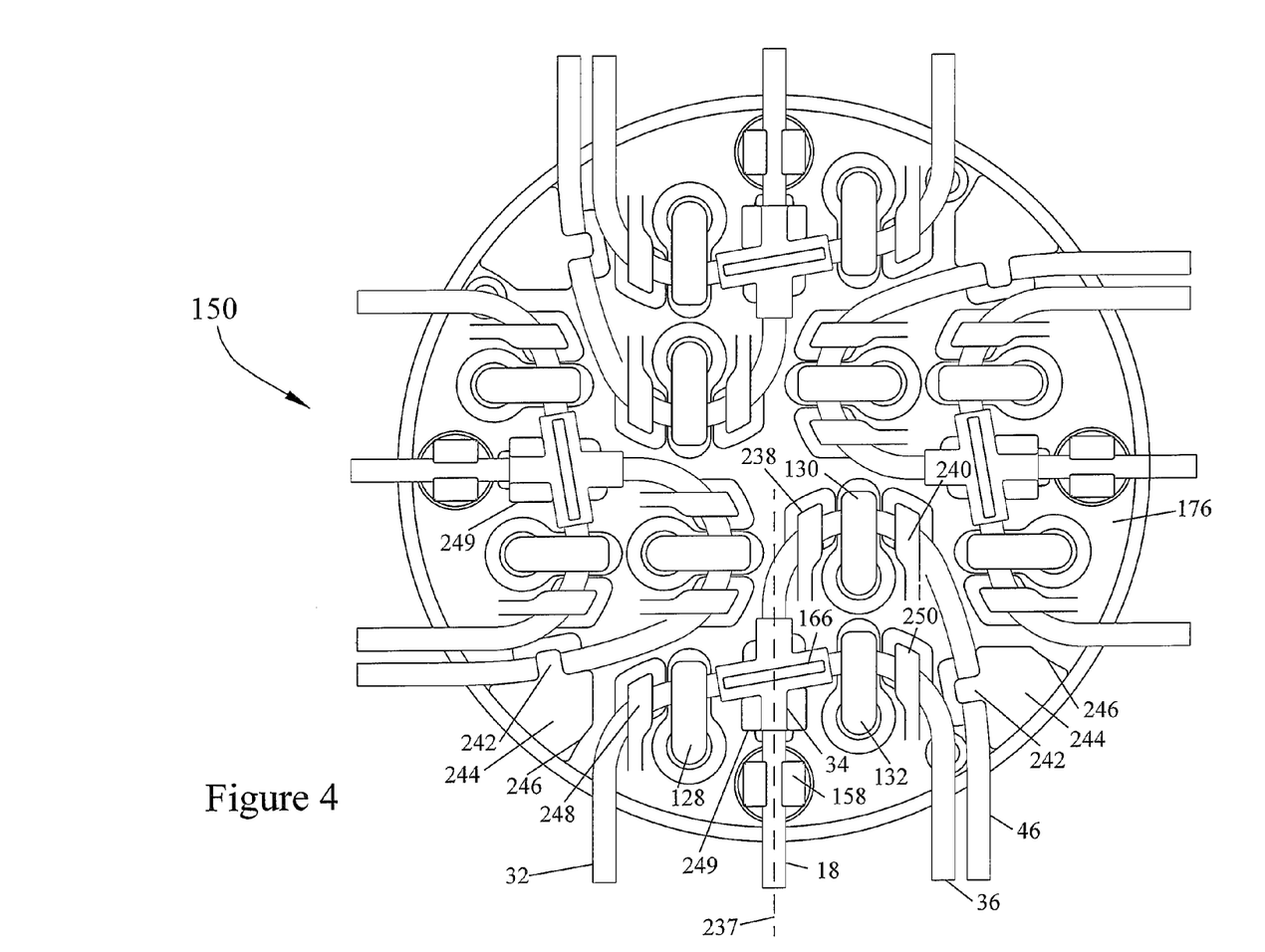
FIG. 4 is a top plan view of an upper plate of the separation apparatus, with four sets of bags connected thereto.
Figure 5:
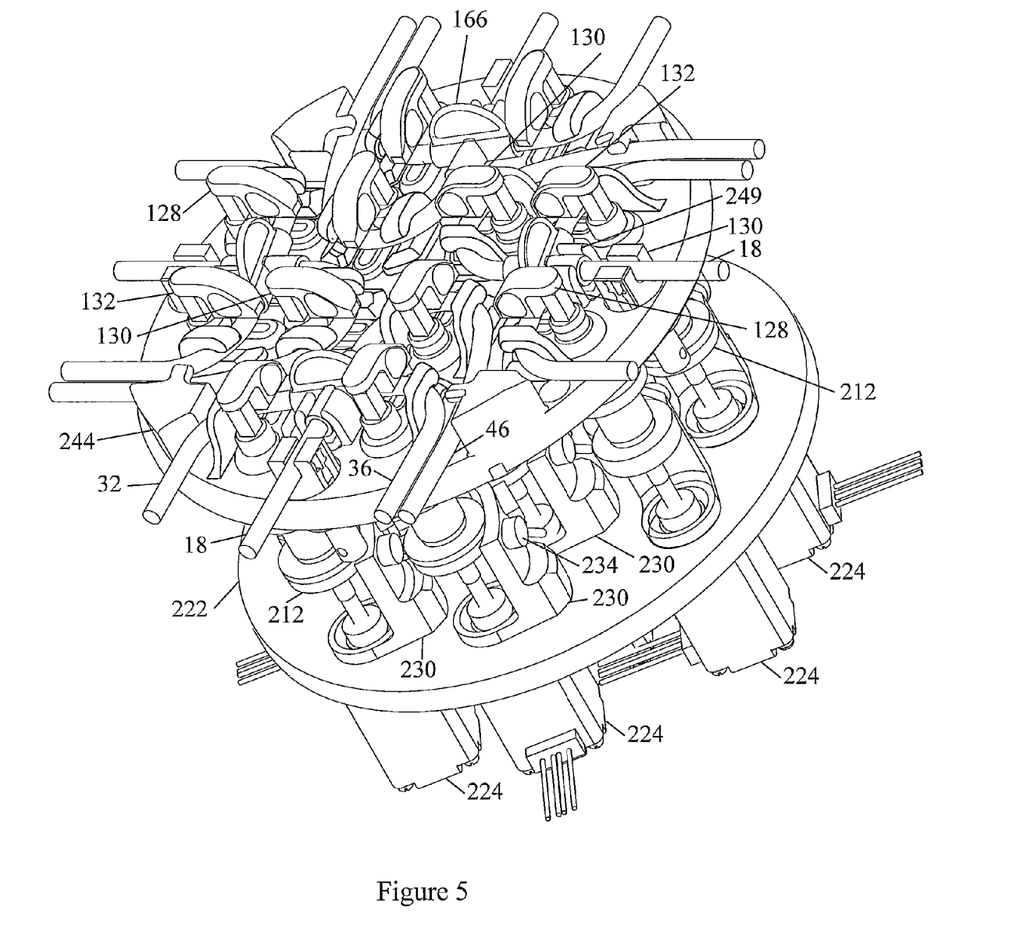
FIG. 5 is a perspective view of a central core of the separation apparatus.

The top plate 176, which supports all four sets of valves, can be seen most clearly in FIG. 4 and FIG. 5. The connector 34 of the bag set 10 lies between a plasma collection valve 128 and a platelet collection valve 132. The tube 18 of the separation bag 12 is placed in the sensor 158 while the waste tube 46 extends radially inwardly to the waste valve 130, which is offset from a radius 237 through the center of the plate 176 and the sensor 158 and which is further linearly aligned with the platelet collection valve 132 on a line parallel to the radius 237. A pair of brackets 238, 240 on either side of the waste valve 130 supports the waste tube 46 under the valve head 136 of the waste valve 130. A circumferential bracket 242 on a guide block 244 keeps the waste tube 46 from straightening radially under centrifugal forces, but rather flows directly into the adjacent cavity 154 where the waste bag 44 is placed. In addition, a bracket 248 adjacent the plasma valve 128 and a bracket 250 adjacent the platelet valve 132 support the plasma tube 32 and the platelet tube 36, respectively. A barrier surface or wall 246 on the guide block constrains the motion of the plasma tube 32, which attempts to straighten radially during processing. The wall 246 keeps the plasma tube slightly bent and directed towards the adjacent cavity 154 where the plasma bag 14 has been placed. The waste tube 46 constrains the platelet tube 36 in a similar manner, preventing the platelet tube 36 from straightening radially and guiding it into the cavity 154. When a bag set is loaded into the centrifuge, the handle 166 on the connector allows the operator to insert the plasma tube 32, waste tube 46 and platelet tube 36 closer to the center of rotation of the centrifuge and then to pull the connector radially outwardly, drawing the tubes into contact with their respective brackets and properly positioning the tubes within their respective valves. The connector 34 is then snapped into a clip 249, which forces the tube 18 into the sensor 158 and holds the tube 18 in position with respect to the sensor 158.

A multiplexing radiofrequency switch 252 (see FIG. 2) is mounted on the bottom of the top plate 176, preferably symmetrically with respect to the axis of rotation 68. A suitable switch is the 5C1 series SP12T switch type available from DowKey Microwave Corporation. As shown schematically in FIG. 9, a primary radiofrequency coil 254 is electrically connected to the multiplexing switch 252. The outputs of the multiplexing switch 252 are electrically connected through balance coils 255 to each of the individual valves 128, 130, and 132. In the illustrated embodiment, four sets 260 of valves, or a total of twelve valves, are shown. The controller 157 is electrically connected to both the RF coil 254 and the multiplexing switch 252 so that radio frequency energy can be developed and delivered to the appropriate valve when it is desired to cut and seal a selected tube.

A representative protocol or process for separating blood into components with the apparatus described above will now be described. According to the representative protocol, four discrete volumes of blood are separated into a plasma component, a first cell component comprising platelets, white blood cells, some red blood cells and a small volume of plasma (later the "buffy coat" component) and a second cell component mainly comprising red blood cells. Each volume of blood is contained in a separation bag 12 of a bag set represented in FIG. 1, in which it has previously been collected from a donor using the collection tube 20. After the blood collection, the collection tube 20 has been sealed and cut close to the separation bag. Typically, the volumes of blood are not the same in the four separation bags 12, and the hematocrit varies from one separation bag to another one. Consequently, the separation bags 12 have slightly different weights.

First stage: Setting the four bag sets in the separation apparatus.

Four separation bags 12 are loaded into the four separation cells 78. The lids 96 are closed and locked, whereby the separation bags 12 are secured by their upper edge in the separation cells 78. The X connectors 34 are inserted over their respective clips 249, which allow the plasma tube 32, the waste tube 46 and the platelet tube 36 to be placed in their brackets as described above. The four plasma component bags 14, the four platelet component bags 16, the four red blood cell component bags 38 and the four filters 40 are inserted in the cavities 154 of the rotor. The pinch valve members 128, 130, 132 are closed and the breakable stoppers 26 in the tubes 18 connecting the separation bags 12 to the X connectors 34 are manually broken.

Second stage: Balancing the rotor in order to compensate for the difference in weights of the separation bags.

At the onset of the second stage, all the pinch valve members 128, 130, 132 are closed. The rotor is set in motion by the centrifuge motor 80 and its rotation speed increases steadily until it rotates at a first centrifugation speed. The pumping station 106 is actuated so as to pump a predetermined overall volume of hydraulic liquid into the four hydraulic chambers 100, at a constant flow rate. This overall volume of liquid is predetermined taking into account the maximum variation of weight between blood donations, so that, at the end of the second stage, the weights in the various separation cells 78 are substantially equal and the rotor is substantially balanced, whatever the specific weights of the separation bags 12 that are loaded in the separation cells 78. Note that this does not imply that the internal cavity 88 of the separation cells 78 should be filled up at the end of the balancing stage. For the purpose of balancing the rotor, it suffices that there is enough hydraulic liquid in the separation cells 78 for equalizing the weights therein, and it does not matter if an empty space remains in each separation cell 78 (the size of this empty space essentially depends on the volume of the internal cavity 88 of a separation cell 78 and the average volume of a blood donation).

Third stage: the blood within the separation bags 12 is sedimented to a desired level.

At the onset of this stage, all pinch valve members 128, 130, 132 are closed. The rotor is rotated at a second centrifugation speed (high sedimentation speed or "hard spin") for a predetermined period of time that is so selected that, whatever the hematocrit of the blood in the separation bags 12, the blood sediments in each of the separation bag 12 at the end of the selected period to a point where the hematocrit of the outer red blood cell layer is about 90 and the inner plasma layer does not substantially contain any cells, the platelets and the white blood cells forming then an intermediary layer between the red blood cell layer and the plasma layer.

Fourth stage: a plasma component is transferred into the plasma component bags 14.

At the onset of this stage, the rotation speed is decreased to a third centrifugation speed, the four first pinch valve members 128 controlling access to the plasma component bags 14 are opened, and the pumping station 106 is actuated so as to pump hydraulic liquid at a first constant flow rate into the hydraulic chambers 100 and consequently squeeze the separation bags 12 and cause the transfer of plasma into the plasma component bags 14. When blood cells are detected by the sensor 158 adjacent the separation cell 78 in which this detection occurs first, the pumping station 106 is stopped and the corresponding first pinch valve member 128 is closed, either immediately or after a predetermined amount of time selected in view of the volume of plasma that it is desirable in the buffy coat component to be expressed in a next stage.

Following the closure of the first (first) pinch valve member 128 (i.e. the first pinch valve of the group of first pinch valve members 128) to close, the pumping station 106 is actuated anew so as to pump hydraulic liquid at a second, lower, flow rate into the hydraulic chambers 100 and consequently squeeze the three separation bags 12 whose outlet is not closed by the corresponding first pinch valve members 128. When blood cells are detected by the sensor 158 in the separation cell 78 in which this detection occurs second, the pumping station 106 is stopped and the corresponding first pinch valve member 128 is closed (same timing as for the closing of the first (first) pinch valve member to close).

Following the closure of the second (first) pinch valve member 128 to close, the pumping station 106 is actuated anew so as to pump hydraulic liquid at the second flow rate into the hydraulic chambers 100 and consequently squeeze the two separation bags 12 whose outlet is not closed by the corresponding first pinch valve members 128. When blood cells are detected by the sensor 158 in the separation cell 78 in which this detection occurs third, the pumping station 106 is stopped and the corresponding first pinch valve member 128 is closed (same timing as for the closing of the first (first) pinch valve member to close).

Following the closure of the third (first) pinch valve member 128 to close, the pumping station 106 is actuated anew so as to pump hydraulic liquid at the second flow rate into the hydraulic chambers 100 and consequently squeeze the separation bag 12 whose outlet is not yet closed by the corresponding first pinch valve member 128. When blood cells are detected by the sensor 158 in the separation cell 78 in which this detection occurs last, the pumping station 106 is stopped and the corresponding first pinch valve member 128 is closed (same timing as for the closing of the first pinch valve member to close).

In the plasma component transfer process described above, the transfer of the four plasma components starts at the same time, run in part simultaneously and stop independently of each other upon the occurrence of a specific event in each separation bag (detection of blood cells by the bag sensor).

Fifth stage: a buffy coat or platelet component is transferred into the platelet component bags 16.

The controller 157 is programmed to start the fifth stage after the four first pinch valve members 128 are closed, upon receiving information from the last sensor 158 to detect blood cells. At the onset of this stage, the rotation speed remains the same (third centrifugation speed), a first of the four second or platelet pinch valve members 132 controlling access to the platelet component bags 16 is opened, and the pumping station 106 is actuated so as to pump hydraulic liquid at a third constant flow rate into the chambers 100 and consequently squeeze the separation bags 12 in the separation cells 78 associated with the opened second pinch valve members 132 and cause the transfer of the platelet component into the platelet component bag 16 connected to this separation bag 12.

After a predetermined period of time after blood cells are detected by the tube sensor 158, the pumping station 106 is stopped and the platelet valve or second pinch valve member 132 is closed. After the first (second) pinch valve member 132 has closed (i.e. the first pinch valve of the group of second pinch valve members 132), a second (second) pinch valve member 132 is opened, and a second platelet component is transferred into a platelet component bag 16, in the same way as above. The same process is successively carried out to transfer the platelet component from the remaining separation bags 12 into the platelet component bag 16 connected thereto.

In the platelet component transfer process described above, the transfers of the four platelet components are successive, and the order of succession is predetermined. However, each of the second, third and four transfers starts following the occurrence of a specific event at the end of the previous transfer (detection of blood cells by the tube sensor 158 or closing of the second valve member 132).

Sixth stage: the red blood cells are washed to remove prions.

In the sixth, or washing, stage, the packed red blood cells remaining in the separation bag 12 are washed one or more times to remove prions—a disease-causing agent that is neither bacterial nor fungal nor viral and contains no genetic material. A prion is a protein that occurs normally in a harmless form. By folding into an aberrant shape, the normal prion turns into a rogue agent. It then co-opts other normal prions to become rogue prions. Prions have been held responsible for a number of degenerative brain diseases, including Creutzfeldt-Jacob disease, fatal familial insomnia, a form of hereditary dementia known as Gertsmann-Straeussler-Scheinker disease, and possibly some cases of Alzheimer's disease. By washing packed red blood cells it is believed that the number of prions, including potentially harmful prions, can be reduced below a harmful level. Level of reduction is dependent on the concentration of red blood cells in the starting condition and the number of wash cycles. For example, if red blood cells are packed to 95 hematocrit in each cycle, it is believed that two (2) wash cycles would remove prions to such a degree that the remaining prions could not replicate sufficiently during a patient's lifetime to cause harm. A hematocrit of 90, in contrast, would require about six (6) wash cycles to achieve the same level of prion elimination.

With the three valves 128, 130, 132 of each set of valves closed, the rotor of the centrifuge slows to a pre-determined low speed. As directed by the controller 157, the pump station 106 withdraws hydraulic fluid from the hydraulic chambers 100. The waste (or third) valve 130 opens, allowing wash solution to flow into the separation bag 12 by action of the centrifugal gravitational field. When sufficient wash solution has drained into the separation bag 12, the waste valve 130 closes and the centrifuge is further slowed. The red blood cell valves 86 are opened. The pump station 106 withdraws additional hydraulic fluid from the hydraulic chambers 100, creating a free surface above the fluids in the separation chamber.

The rotor is then controlled so as to oscillate back and forth around the rotation axis 68 for a determined period of time, at the end of which the cells in the separation bags 12 are substantially suspended in wash solution with a small amount of residual plasma. The rotor is then set in motion again by the centrifuge motor 80 so that its rotation speed increases steadily until it reaches the fourth centrifugation speed (low sedimentation speed or "soft spin"). The rotor is rotated at the fourth rotation speed for a predetermined period of time that is selected so that the blood components in the separation bags 12 at the end of the selected period are separated to a point where the separation bags 12 exhibit an outer layer comprising packed red blood cells and an inner annular layer substantially comprising wash solution with dilute plasma.

A first valve of the four waste (or second) pinch valves 130 controlling access to the waste bags 44 is opened, and the pumping station 106 is actuated so as to pump hydraulic liquid at a constant flow rate into the hydraulic chambers 100 and consequently squeeze the separation bag 12 in the separation cell 78 associated with the opened waste valve 130 and cause the transfer of the used wash solution into the waste bag 44 connected to this separation bag 12. When blood cells are detected by the tube sensor 158 near the separation cell 78 associated with the opened waste valve 130, the pumping station 106 is stopped and the waste valve 130 is closed. After the first of the waste valves 130 has closed (i.e. the first pinch valve of the group of waste valves 130), a third one of the set of waste valves 130 is opened, diametrically across from the first of the waste valves, and used wash solution is transferred into a waste bag 44, in the same manner as above.

The same process is successively carried out to transfer the used wash solution from the two remaining separation bags 12 into the waste bag 44 connected thereto, beginning with a second waste valve 130 orthogonal to the first and third waste valves and ending with a fourth waste valve diametrically across from the second waste valve.

Seventh stage: the centrifugation process is ended.

The controller 157 is programmed to start the seventh stage after the four waste valve members 130 are closed, upon receiving information from the last tube sensor 158 to detect blood cells. The rotation speed of the rotor is decreased until the rotor stops, the pumping station 60 is actuated so as to pump the hydraulic liquid from the hydraulic chambers 100 at a high flow rate until the hydraulic chambers 100 are empty, and the valve members 128, 130, and 132 are actuated so as to seal and cut the tubes 32, 36, 46. The red blood cells remain in the separation bags 12. When the seventh stage is completed, the four bag sets are removed from the separation apparatus and each bag set is separately handled manually.

The breakable stopper 28 blocking the communication between the separation bag 12 and the tube 22 connected thereto is broken. The storage solution contained in the RBC component bag 38 is allowed to flow by gravity through the leuko-reduction filter 40 and into the separation bag 12, where it is mixed with the red blood cells so as to lower the viscosity thereof. The content of the separation bag 12 is then allowed to flow by gravity through the filter 40 and into the RBC component bag 38. The white blood cells are trapped by the filter 40, so that substantially only red blood cells are collected into the RBC component bag 38.

It will be apparent to those skilled in the art that various modifications can be made to the apparatus and method described herein. Thus, it should be understood that the invention is not limited to the subject matter discussed in the specification. Rather, the present invention is intended to cover modifications and variations.

The invention claimed is:

1. An apparatus for separating at least two discrete volumes of whole blood into at least a first component and a second component comprising
 a centrifuge rotor adapted to rotate about a rotation axis,
 at least one separation cell, adapted to receive a separation bag of a set of fluidly interconnected bags, said set comprising at least said separation bag containing a volume of whole blood, and at least one component bag,
 a cavity adapted to receive at least said component bag,
 a plurality of valves mounted on the centrifuge rotor, the valves being adapted to control fluid flow between parts of the set of interconnected bags, each of said valves comprising
  a spring-loaded valve section comprising
   a jaw mounted on a shaft, wherein said jaw is adapted to apply radio frequency energy to an adjacent tube to seal the tube, and
   a spring adapted to move said jaw into a closed position,
  a stepper motor section adapted to push against said shaft to move said jaw into an open position, said stepper motor section being mechanically and electrically disconnected from said shaft whenever said jaw is in a closed position and during radio frequency welding of the tube, and
  a controller electrically connected to said stepper motor section.

2. The apparatus of claim 1, wherein said valve section is mounted on an upper plate and said stepper motor section is mounted on a lower plate.

3. The apparatus according to claim 2, wherein said valve section comprises an anvil under said jaw, said anvil being coupled to a source of radio frequency energy.

4. The apparatus according to claim 2 wherein said valve section further comprises a compression assembly for attaching said valve section to said upper plate.

5. The apparatus according to claim 2 further comprising a pair of position sensors mounted on said lower plate and means attached to said valve section for activating said position sensors in response to changes in position of said jaw.

6. The apparatus according to claim 1, wherein the spring is coupled to said shaft and is adapted to maintain said jaw in contact with said tube as said tube is sealed.

7. The apparatus of claim 6, further comprising a main radio frequency coil selectively electrically coupled to each of said valves through a multiplexing switch.

8. The apparatus of claim 7 wherein each of said valves is electrically connected to said multiplexing switch through a balancing coil.

* * * * *